United States Patent
DeFreitas et al.

(10) Patent No.: US 6,663,900 B2
(45) Date of Patent: Dec. 16, 2003

(54) MICROCAPSULES HAVING HIGH CAROTENOID CONTENT

(75) Inventors: Zoraida DeFreitas, Polk City, IA (US); Harlan Hall, Verona, WI (US); Jerry Newman, West Des Moines, IA (US); Mike Gordon, Arlington, TX (US)

(73) Assignee: Kemin Foods, LC, Des Moines, IA (US)

( * ) Notice: Subject to any disclaimer, the term of this patent is extended or adjusted under 35 U.S.C. 154(b) by 0 days.

(21) Appl. No.: 10/062,359

(22) Filed: Feb. 1, 2002

(65) Prior Publication Data

US 2003/0148099 A1 Aug. 7, 2003

(51) Int. Cl.⁷ .............................. A61K 9/16; B32B 15/02
(52) U.S. Cl. .................. 424/492; 264/4.1; 264/4.3; 264/213.3; 264/213.35; 428/402.24; 428/403; 424/489; 424/490; 424/491; 424/493
(58) Field of Search ................ 264/4.1, 4.3; 427/213.3, 427/213.35; 428/402.24, 403; 424/489, 490, 491, 492, 493

(56) References Cited

U.S. PATENT DOCUMENTS 5,780,056 A    7/1998    Akamatsu et al.
5,972,985 A    10/1999   Thomas et al.

OTHER PUBLICATIONS

Murphy, Patricia A., "Technology of Vitamin A Fortification of Foods in Developing Countries", *Food Technology*, Sep. 1996, Institute of Food Technologists, Chicago, IL.

Seddon, et al., *J. Amer. Medical Association*, 1994, 272 (18): 1413–1420.

*Primary Examiner*—Samuel A. Acquah
(74) *Attorney, Agent, or Firm*—Kent Herink; Daniel Rosenberg; Davis Law Firm

(57) ABSTRACT

Microcapsules having a carotenoid content of between about 10% and 50% by weight. A crystalline form of one or more carotenoids is processed in a fluidized bed coating machine where a protective coating of a sugar or polyhydric alcohol, a starch, and optionally a protein, is applied. The carotenoid content of the finished microcapsules is in excess of 80% of the carotenoids present in the starting material.

11 Claims, No Drawings

//MICROCAPSULES HAVING HIGH CAROTENOID CONTENT

BACKGROUND OF THE INVENTION

The invention relates generally to microencapsulated carotenoid compounds and, more particularly, to microcapsules having a carotenoid content in the range of between about 5% and about 20% by weight that are suitable for addition to food and personal care products and to dietary supplements, typically in the form of tablets or capsules.

Carotenoids are naturally-occurring yellow to red pigments of the terpenoid group that can be found in plants, algae, bacteria, and certain animals, such as birds and shellfish. Carotenoids include hydrocarbons (carotenes) and their oxygenated, alcoholic derivatives (xanthophylls). They include actinioerythrol, astaxanthin, bixin, canthaxanthin, capsanthin, capsorubin, β-8'-apo-carotenal (apo-carotenal), β-12'-apo-carotenal, a-carotene, β-carotene, "carotene" (a mixture of α- and β-carotenes), γ-carotene, β-cryptoxanthin, lutein, lycopene, violerythrin, zeaxanthin, and esters of hydroxyl- or carboxyl-containing members thereof. Many of the carotenoids occur in nature as cis- and trans-isomeric forms, while synthetic compounds are frequently racemic mixtures.

Carotenoids are valuable as pigments and as biologically active compounds. Carotenoids are used in the food, personal care, pharmaceutical industries and nutritional supplements, most commonly to date because of their health benefits. The carotenoids have been extensively studied for their effect on various chronic diseases, such as age-related macular degeneration, skin cancer and heart disease. Among the dietary carotenoids, the focus has been on β-carotene because of its pro-vitamin A activity. However, many research studies have elicited the broad role that other carotenoids play in human and animal health. The xanthophylls in particular have been shown to possess strong antioxidant activities and may be useful in protecting humans from certain diseases. For example, lutein and zeaxanthin are reddish-orange pigments that have been inversely correlated with reduction of risk for macular degeneration (Seddon et al., 1994. *J. Amer. Med. Assoc.* 272(18): 1413–1420); lycopene is a red pigment that has been implicated in a reduced risk of prostate cancer.

The attractiveness of carotenoids as pigments is at least partially due to the carotenoids being naturally occurring compounds. Carotenoids have long been used in the poultry industry to improve the appearance of broiler's skin and egg yolks. In foods and beverages, carotenoids, such as β-carotene, are added to replace artificial colors and to increase their nutritional value.

One area in which carotenoids are being used is in human multivitamin/multimineral products and dietary supplements, where they are typically added to tablet or capsule formulations. A problem with the use of carotenoids in food and personal care products, including supplement tablets, is the degradation of most carotenoids upon exposure to heat, oxygen, and light. Degradation will be accelerated at the elevated pressures used in tabletting. Typically a slight overage (10–30%) of the initial amount of the carotenoid is added to the tablet to meet the level desired allowing for losses during formation of the tablet. One method currently used commercially to increase the stability of the carotenoids is to microencapsulate the carotenoids in concentrations up to 10%. The inert coating materials increase the stability of the carotenoids during both the formation and shelf life of the tablet.

A consideration of tablet formulators is the volume of the tablet that must be swallowed by the consumer. Particularly with so-called multi-vitamin/multi-mineral products, a decision whether or not to add a particular new ingredient to a formulation already containing a large number of ingredients may depend on the additional volume of material that must be added to the tablet in order to include the new ingredient. Obviously, the higher the active ingredient content in the new product being added to the tablet formulation, the less volume of material that must be added.

The prior art has attempted to address the heat and oxygen lability of the carotenoids by encapsulating the carotenoid source with a coating material mix in a fluidized bed, spray dryer, or similar microencapsulation process. While the resistance to losses of active ingredient during tabletting and after tabletting (shelf-life) can be increased with prior art microencapsulation techniques, these techniques are known to result in a loss in activity during microencapsulation and further do not permit higher than up to about 5 to 10% of the carotenoid in the microcapsule or beadlet. Tabletting is also known to be inimical to the integrity of certain microcapsules, resulting in exposure of the carotenoid to oxygen and metals or minerals acting as oxidation catalysts in the environment of the tablet.

There is a need for microcapsules or beadlets of carotenoids that contain high amounts of the carotenoid, are formed by a process which preferably limits the loss of carotenoid during formation of the microcapsule, and provide a coating which protects the carotenoid from losses during manufacture or processing of the food, dietary supplement or personal care product.

SUMMARY OF THE INVENTION

The invention consists of coated microcapsule of one or more carotenoids that have a carotenoid content of between about 10% and about 50% by weight. The microcapsules are formed using a fluidized bed coating machine that produces minimal losses in carotenoid activity during the microencapsulation process. Microcapsules produced by the process will release the encapsulated carotenoids upon ingestion and are suitable for addition to food, multivitamins, dietary supplements and personal care products. The microcapsules also survive tabletting substantially intact and protect the activity of the encapsulated carotenoids during tabletting and during storage of the tablet or other food or personal care product prior to consumption or use by the consumer.

The carotenoid used as a starting material in the process is preferably a pure or crystalline form of the carotenoid as opposed to an oil suspension or the like where the carotenoid content of the starting material is already diluted. In one form of the process, the carotenoid-containing starting material is added to a fluidized bed dryer and the flow of heated air is started. A liquid coating material is sprayed on to the fluidized bed of the carotenoid. The coating material consists of an aqueous solution of a sugar or sorbitol, a starch or maltodextrin, and optionally a coating protein such as gelatin. The liquid coating material is applied to the carotenoid in the dryer until the moisture-adjusted weight has been added to equal the target formulation of the microcapsule being formed. In an alternative form of the process, the sugar or other inert material is suspended in the fluidized bed dryer and the carotenoid is added to the aqueous solution of the starch/maltodextrin, or starch/maltodextrin and gelatin, and sprayed on the sugar. It has surprisingly been found that, even though the initially unprotected carotenoid is exposed to elevated temperatures (between about 150° and about 200° F.) in an oxygen-rich (i.e., air) atmosphere, essentially no loss in activity of the carotenoid is found when the microcapsule are measured immediately after the microencapsulating process, and after extended storage periods of the microcapsules at temperatures up to 100° F.

Microscopic examination of tablets formed using conventional tabletting techniques showed that the microcapsules remained substantially intact and that the coating material protected the encapsulated carotenoid against degradation during tabletting.

Carotenoids most suitable for incorporation in microcapsules of the present invention include those carotenoids known to be especially heat, oxygen, or light labile, specifically lutein, β-carotene, β-cryptoxanthin, canthaxanthin, α-carotene, lycopene, and zeaxanthin. These carotenoids may be included in the microcapsules either individually or in combinations of two or more.

An object of the present invention is to provide a stable carotenoid-containing product with high levels of carotenoid for use in the formulation of tablets and capsules and in the addition to food and personal care products.

Another object of the invention is to provide a microcapsule or beadlet of a coated carotenoid that will allow dietary supplement manufacturers to include higher levels of the active material without adding excessive amounts of inert coating materials.

A further object of the invention is to provide a microcapsule or beadlet of a coated carotenoid that may include a single carotenoid or mixtures of two or more carotenoids at various pre-selected levels.

Still another object of the invention is to provide a microcapsule manufactured by a method that causes only minimal losses of activity during processing and results in a product with an extended shelf life.

These and other objects of the invention will be appreciated by those skilled in the art upon a review of this specification and the appended claims.

DETAILED DESCRIPTION OF A PREFERRED EMBODIMENT

The microcapsules of the present invention are microcapsules of one or more carotenoids which has been surrounded by a protective coating which protects the carotenoid against degradation by oxygen, heat, and light. The microcapsules have a carotenoid content of between about 10% and about 50% by weight.

The carotenoids included in the microcapsule include all naturally occurring or synthetic carotenoids that are subject to degradation during processing, incorporation in a food, dietary supplement or personal care product, or during storage. The carotenoids may be incorporated individually in the microcapsule or in combinations of two or more carotenoids in any desired relative amounts. Carotenoids particularly suited for incorporation into the microencapsulated microcapsule include lutein, β-carotene, β-cryptoxanthin, canthaxanthin, α-carotene, lycopene, and zeaxanthin.

The coating material includes a sugar or polyhydric alcohol such as sorbitol and a starch or maltodextrin, and may include a coating protein. In some preferred examples, the coating material comprises a water-soluble or gelation type gelatin, such as beef, pork, or fish gelatin. The unhydrolyzed gelatin should have a gel strength of between about 180 and about 220 Blooms, and may include either or both Type A (low pH) or Type B (high pH)- gelatins. A preferred gelatin is Type A fish gelatin, certified as Kosher. Gelatin is included in the coating material in an amount between about 0 and about 20 percent by weight.

Sugars suitable for use in the coating material include mono- and oligosaccharides. Specific sugars include glucose, fructose, galactose, sucrose, and lactose. The amount of sugar included in the coating material is between about 10 and about 50 percent by weight. Preferred sugars include sucrose. Polyhydric alcohols, carbohydrate derivatives, such as sorbitol, or glycerol may be used in combination with the sugars, or in place of the sugars to make microcapsules which are sugar-free. The amount of polyhydric alcohol included in the coating material is between about 10 and about 20 percent by weight. The preferred polyhydric alcohol is sorbitol.

A starch or dextrin is also included in the coating material. Exemplary starches include food starches derived from corn, potatoes, rice, tapioca, or wheat. Exemplary dextrins include maltodextrin. A preferred starch is—a modified food starch derived from tapioca and sold by National Starch and Chemical Company under the trademark CAPSUL® TA. Starch and/or dextrin are included in the coating material in an amount between about 20 and about 40 percent by weight.

The microcapsules of the present invention are formed by an air suspension technique whereby a coating is applied to suspended particles. Such air suspension technique can be any technique that is classified as an air suspension method and which is able to apply a satisfactory coating without substantial loss of activity of the carotenoid particles being coated. An example of such an air suspension technique is the Wurster process that takes place in a fluid bed dryer. In the Wurster process, particles to be coated are separated from each other while suspended in an air or gas stream and sprayed with a coating formulation while they are suspended. The process takes place in a modified fluid bed that includes a fluid bed bowl situated at the lower end of a chamber that is divided into two sections. High velocity air is directed upwardly form a central location of the fluid bed bowl. The particles are entrained in the air stream in the inner section of the chamber, where there is created a high velocity zone that separates the particles and pneumatically transports them in a vertical direction. One or more spray nozzles for spraying of the coating formulation direct the formulation onto the vertically moving particles. After passing the nozzle, the particles enter the expanded section of the chamber, where the velocity of the air stream has slowed, and they fall back down into the outer section of the fluid bed bowl. The coating material dries while the particles are suspended and separated to prevent agglomeration from occurring. The coated particles—remain fluidized enough to allow them to continue moving towards the bottom of the bowl. When the particles reach the bottom, they are drawn back into the high velocity air stream and the cycle is repeated. The process continues until the desired level of coating has been achieved.

Method of Analysis of Carotenoid and Lutein Content

The microcapsules made in accordance with the present invention are analyzed for carotenoid content. This method of analysis requires use of samples that will yield no more than about 5 to 7 mg of carotenoids. Accordingly, the amount of sample added at the start of the method is selected to have an expected yield in this range. If using a microcapsule that is expected to contain 10% by weight carotenoids, a 75 mg sample of the microcapsule is weighed and added to a 50 ml glass centrifuge tube with a stopper; if using a microcapsule that is expected to contain 25% carotenoids, a 30 mg sample is weighed and added to a 50 ml glass centrifuge tube with stopper; and so on. Approximately 20 ml of 0.1 M EDTA/2NaH$_2$O (37.224 g/L) is added. The stopper is placed on the tube and the tube is heated in a 60° C. water bath for 20 minutes. The tube is removed from the water bath and sonicated for 15 minutes with occasional swirling of the tube. The tube is allowed to cool to room temperature and then 30 ml of methylene chloride is added by pipette. The stopper is added and the contents mixed by repeated inversion, and frequent removal of the stopper for venting. The tube is placed in the dark and the layers are allowed to separate, approximately 30 minutes. A pipette is used to draw off the top water layer, which is discarded. Between 2 and 3 g of sodium sulfate are added to the methylene chloride layer and the stopper replaced and the tube shaken gently. The sodium sulfate is allowed to settle and 1 ml of the methylene chloride layer is removed by pipette and added to a 100 ml volumetric flask and diluted to the mark with ethanol. The ethanol mixture is placed in an UV/Vis Specrophotometer (Agilent, Palo Alto, Calif.), which has previously been zeroed against ethanol. Absorbance at 446 nm is read. The percentage of total carotenoids is determined according to the following formula:

$$\% \text{ Total Carotenoids} = \frac{(\text{Abs} @ \; 446 \text{ nm} \times \text{methylene chloride vol. (ml)} \times \text{EtOH vol. (ml)})}{(2250 \times \text{sample mass } (g))}$$

For the HPLC analysis, 1 ml of solution A is filtered through a 0.45 micron syringe filter into a HPLC sample vial. This sample is dried down using a nitrogen stream and then the solids are dissolved in a 75:25 solution of hexane/ethylacetate. This solution is sonicated for 2 minutes and this sample is injected on the HPLC using a silica column (Agilent, Palo Alto, Calif.) with isocratic elution (75:25 hexane/ethylacetate) and detection at 446 mn and the percent area of the lutein peak is determined.

Lutein %=(total carotenes %×HPLC percent area for Lutein)

Production Process

The process was carried out using a 4"/6" portable fluid bed coater from Coating Place, Inc., Verona, Wis. The coater has a capacity of between 0.60 and 1.7 L per batch. The source of carotenoids was FloraGLO® Brand Crystalline Lutein from Kemin Industries, Inc., Des Moines, Iowa (referred to herein as "dry cake"). This source of carotenoids was analyzed and a typical result showed the product to include 85% carotenoids (78% lutein, 5% zeaxanthin, and 2% other carotenoids), 8% paraffin waxes, and 1% fatty acid as palmitate.

EXAMPLE 1

An experiment was conducted to coat dry cake with a mixture of fish gelatin, starch, and sucrose at a target level of 38% carotenoids and 21% lutein by weight. The coater was charged with 250 g of dry cake. A coating mixture was prepared comprising 900 g of 25% Capsul® TA (from 250 g Capsul TA dissolved in 750 g purified water heated to 160° F. while stirring); 250 g of 50% sucrose (from 125 g sucrose dissolved in 125 g purified water heated while stirring to dissolve the sucrose); 125 g fish gelatin (Rousellot 200A FE 8) dissolved in 425 g purified water, heated to 120° F. while stirring to dissolve the gelatin; and 25 g of Vitamin E acetate 50% CWD and 25 g of Vitamin A (VSP 1% tocopherol), both from BASF. The coater was adjusted to provide heated fluidizing air at 180° F. at a volume of 13–14 cubic feet per minute. The coating was sprayed operating the pump at 6.2–6.6 rpm. The coater was run until 38% and 21% theoretical total carotenoid content was reached. The microcapsules were analyzed using the Method of Analysis of Carotenoid and Lutein Content set out above. The microcapsules were found to have a measured amount of 37.9% and 22.6% carotenoid compared to the 38% and 21% carotenoid content determined by using the certificate of Analysis from a typical dry cake lot. Accordingly, there was essentially no loss of carotenoid content during the process. The lutein content in the above samples were 33.17% and 19.71%, respectively, which also shows that essentially no lutein was lost during the process.

EXAMPLE 2

An experiment was conducted to coat dry cake with a mixture of fish gelatin, maltodextrin, and sorbitol at a target level of 21% carotenoids by weight. The coater was charged with 350 g of dry cake. A coating mixture was prepared comprising 1172 g of purified water, 225 g of Maltrin® M100 maltodextrin (Grain Processing Corp., Muscatine, Iowa), 179 g of 70% sorbitol, 125 g fish gelatin (Rousellot 200A FE 8), and 25 g of Vitamin E acetate 50% CWD and 25 g of Vitamin A (VSP 1% tocopherol), both from BASF. The coater was adjusted to provide heated fluidizing air at 180° F. at a volume of 25 cubic feet per minute. The coating was sprayed operating the pump at 7.0 rpm. The coater was run for a total of approximately 6 hours and resulted in 501 g of microcapsule. The microcapsules were analyzed using the Method of Analysis of Carotenoid and Lutein Content set out above. The microcapsule were found to have a measured amount of 22.87% total carotenoids and 20.25% lutein compared to the calculated 21.25% carotenoids and 19.5% lutein content determined by using the certificate of Analysis from a typical dry cake lot. In other words, there was an insignificant loss of lutein in the process.

EXAMPLE 3

An experiment was conducted to coat crystallized sucrose with a mixture of lutein dry cake, Capsul® TA, and sucrose, along with Vitamin A and Vitamin E at a target level of 13% carotenoids by weight. The coater was charged with 260 g of sucrose. A coating mixture was prepared comprising 1000 g of purified water and 230 g of Capsul® TA. The mixture was heated to 160° C. while stirring. Then, 96 g of sucrose, 104 g lutein dry cake, and 16 g of Vitamin E acetate 50% CWD and 16 g of Vitamin A (VSP 1% tocopherol), both from BASF, were added. The coater was adjusted to provide heated fluidizing air at 180° F. at a volume of 18 cubic feet per minute. The coating was sprayed operating the pump at 6.8 rpm. The coater was run for a total of approximately 3 hours and resulted in 585 g of microcapsule. The microcapsules were analyzed using the Method of Analysis of Carotenoid and Lutein Content set out above. The microcapsule were found to have a measured amount of 8.20% total carotenoids and 7.49% lutein compared to the calculated 11.0% carotenoids and 10.14% lutein content determined by using the certificate of Analysis from a typical dry cake lot. In other words, there was an insignificant loss of lutein in the process.

| Prototype | Time point | Days | % Carotenoids | % Lutein | % Zeaxanthin |
|---|---|---|---|---|---|
| Example 3 | Initial | 1 | 8.2 | 7.49 | 0.51 |
| gelatin free | Week 1 | 6 | 8.34 | 7.65 | 0.5 |
| tapioca starch | Week 3 | 19 | 9.35 | 8.21 | 0.51 |
| sucrose core | Month 1 | 26 | 7.5 | 6.81 | 0.48 |
| | Month 2 | 53 | 9.35 | 8.61 | 0.57 |

EXAMPLE 4

An experiment was conducted to coat crystallized sucrose with a mixture of lutein dry cake, Capsule TA, sucrose and fish gelatin, along with Vitamin A and Vitamin E at a target level of 13% carotenoids by weight. The coater was charged with 260 g of sucrose. A coating mixture was prepared comprising 934 g of purified water, 141 g of Capsul® TA and 68 g fish gelatin. The mixture was heated to 160° C. while stirring. Then, 79 g of sucrose, 87 g lutein dry cake, and 14 g of Vitamin E acetate 50% CWD and 14 g of Vitamin A (VSP 1% tocopherol), both from BASF, were added. The coater was adjusted to provide heated fluidizing air at 180° F. at a volume of 24 cubic feet per minute. The coating was sprayed operating the pump at 6.5 rpm. The coater was run for a total of approximately 4.4 hours and resulted in g of microcapsule. The microcapsules were analyzed using the Method of Analysis of Carotenoid and Lutein Content set out above. The microcapsule were found to have a measured amount of 11.48% total carotenoids and 9.89% lutein compared to the calculated 11.8% carotenoids and 9.88% lutein content determined by using the certificate of Analysis from a typical dry cake lot. In other words, there was no loss of lutein in the process. The stability of these microcapsules was excellent, providing up to 2 months of storage at 100° F.

| Prototype | Time point | Days | % Carotenoids | % Lutein | % Zeaxanthin |
|---|---|---|---|---|---|
| Example 4 | Initial | 1 | 11.48 | 9.89 | 0.71 |
| low fish gelatin | Day 3 | 3 | 11.54 | 10.49 | 0.69 |
| tapioca starch | Week 1 | 7 | 11.46 | 9.76 | 0.65 |
| sucrose | Week 2 | 14 | 10.46 | 9.09 | 0.45 |
| sucrose core | Month 1 | 31 | 9.95 | 8.91 | 0.54 |
| | Month 2 | 62 | 10.13 | 9.12 | 0.59 |
| | Month 3 | 116 | 8.37 | 7.66 | 0.46 |

EXAMPLE 5

An experiment was conducted to coat crystallized sucrose with a mixture of lutein dry cake, Capsul® TA, and sorbitol, along with citric and ascorbic acids at a target level of 13% carotenoids by weight. The coater was charged with 260 g of sucrose. A coating mixture was prepared comprising 1000 g of purified water and 230 g of Capsul® TA. The mixture was heated to 160° C. while stirring. Then, 123 g of sorbitol (70%), 104 g lutein dry cake, and 16 g of citric acid and 16 g of ascorbic acid were added. The coater was adjusted to provide heated fluidizing air at 147–157° F. at a volume of 20–26 cubic feet per minute. The coating was sprayed operating the pump at 0–4.0 rpm. The coater was run for a total of approximately 104 minutes and resulted in 390 g of microcapsule. The microcapsules were analyzed using the Method of Analysis of Carotenoid and Lutein Content set out above. The microcapsule were found to have a measured amount of 8.88% total carotenoids and 8.09% lutein compared to the calculated 11.18% carotenoids and 9.88% lutein content determined by using the certificate of Analysis from a typical dry cake lot. In other words, there was an insignificant loss of lutein in the process.

| Prototype | Time point | Days | % Carotenoids | % Lutein | % Zeaxanthin |
|---|---|---|---|---|---|
| Example 5 | Initial | 1 | 8.88 | 8.09 | 0.57 |
| gelatin free | Week 1 | 8 | 9.73 | 8.89 | 0.61 |
| tapioca starch | Month 1 | 28 | 10.44 | 9.29 | 0.84 |

EXAMPLE 6

An experiment was conducted to coat maltodextrin with a mixture of lutein dry cake, Capsul® TA, and sorbitol, along with citric and ascorbic acids at a target level of 13% carotenoids by weight. The coater was charged with 300 g of Maltrin®. A coating mixture was prepared comprising 1000 g of purified water, 248 g of Maltrin® and 103 g of sorbitol (70%), 104 g lutein dry cake, 13.5 g of citric acid and 13.5 g of ascorbic acid. The coater was adjusted to provide heated fluidizing air at 177° F. at a volume of 14–15 cubic feet per minute. The coating was sprayed operating the pump at 3.2 rpm. The coater was run for a total of approximately 4 and one-half hours and resulted in 439 g of microcapsule. The microcapsules were analyzed for up to two months using the Method of Analysis of Carotenoid and Lutein Content set out above. The microcapsule were found to have a measured amount of 9.7% total carotenoids and 8.9% lutein compared to the calculated 11.18% carotenoids and 9.88% lutein content determined by using the certificate of Analysis from a typical dry cake lot. In other words, there was an approximately 12% loss of lutein in the process. However, the microcapsules remained stable for 26 days at 100 F.

| Prototype | Time point | Days | % Carotenoids | % Lutein | % Zeaxanthin |
|---|---|---|---|---|---|
| Example 6 | Initial | 1 | 8.61 | 7.74 | 0.6 |
| gelatin free | Week 1 | 6 | 7.57 | 6.77 | 0.49 |
| maltodextrin | Week 3 | 19 | 8.81 | 7.9 | 0.57 |
| sorbitol, | Month 1 | 26 | 8.9 | 8.08 | 0.58 |
| lutein core | Month 2 | 53 | 7.45 | 6.68 | 0.50 |

EXAMPLE 7

An experiment was conducted to coat dry cake with a mixture of fish gelatin, maltodextrin, and sorbitol at a target level of 25.6% carotenoids by weight. The coater was charged with 300 g of dry cake. A coating mixture was prepared comprising 337 g of purified water, 491 g of Maltrino M100 maltodextrin (Grain Processing Corp., Muscatine, Iowa), 389 g of 70% sorbitol, 273 g fish gelatin (Rousellot 200A FE 8), 0.75 g citric acid, 0.12 g ascorbic acid, and 7.5 g of Vitamin E acetate 50% CWD from BASF. The coater was adjusted to provide heated fluidizing air at 180° F. at a volume of 14 cubic feet per minute. The coating was sprayed operating the pump at 6.0–6.3 rpm. The coater was run for a total of approximately 9 and one-half hours and resulted in 1091 g of microcapsule. The microcapsules were analyzed eight and twenty-eight days later using the Method of Analysis of Carotenoid and Lutein Content set out above. The microcapsule were found to have a measured amount of 23.1% total carotenoids and 21.0% lutein compared to the calculated 25.6% carotenoids and 20% lutein content determined by using the certificate of Analysis from a typical dry cake lot. In other words, there was no loss of lutein in the process. A 17% loss in lutein content was seen in this prototype after storage at 100° F. for one month.

| Prototype | Time point | Days | % Carotenoids | % Lutein | % Zeaxanthin |
|---|---|---|---|---|---|
| Example 7 | Initial | 1 | 23.1 | 21.03 | 1.47 |
| fish gelatin | Week 1 | 8 | 20.65 | 18.84 | 1.30 |
| sorbitol | Month 1 | 28 | 19.77 | 17.41 | 1.68 |

The foregoing descriptions comprise illustrative embodiments of the present inventions. The foregoing embodiments and the methods described herein may vary based on the ability, experience, and preference of those skilled in the art. Merely listing the steps of the method in a certain order does not necessarily constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A microcapsule of one or more crystalline forms of carotenoids comprising a protective coating that releases the carotenoids upon ingestion of the microcapsule and wherein the carotenoid content of the microcapsule is between about 5% and about 20% by weight.

2. A microcapsule as defined in claim 1, wherein the coating comprises a sugar or polyhydric alcohol, a starch or dextrin, and optionally a protein.

3. A microcapsule as defined in claim 2, wherein the protein comprises gelatin.

4. A microcapsule as described in claim 2, wherein the sugar is selected from the group consisting of glucose, fructose, galactose, sucrose, and lactose, the dextrin is maltodextrin, and the polyhydric alcohol is selected from the group consisting of sorbitol and glycerol.

5. A microcapsule as described in claim 1, wherein the carotenoids comprise one of more of the group consisting of actinioerythrol, astaxanthin, bixin, canthaxanthin, capsanthin, capsorubin, β-8'-apo-carotenal (apo-carotenal), β-12'-apo-carotenal, α-carotene, β-carotene, "carotene" (a mixture of α- and β-carotenes), γ-carotene, β-cryptoxanthin, lutein, lycopene, violerythrin, zeaxanthin, and esters of hydroxyl- or carboxyl-containing members thereof.

6. A microcapsule as described in claim 5, wherein the carotenoids are comprised of crystalline forms absent substantial amounts of oil.

7. A method of forming a microcapsule of one or more crystalline forms of carotenoids having a protective coating that releases the carotenoids upon ingestion of the microcapsule, comprising the steps of:

(a) fluidizing a carotenoid-containing starting material in a coating machine to produce a recirculating flow of the carotenoid-containing starting material;

(b) preparing a liquid coating material comprising a sugar, a starch or maltodextrin, and optionally a coating protein; and (c) spraying the liquid coating material onto the recirculating carotenoid-containing starting material to build up the protective coating on the starting material.

8. A method as defined in claim 7, wherein the amount of carotenoids present in the microcapsule is greater than 80% of the amount of carotenoids in the starting material.

9. A method as defined in claim 7, wherein the sugar is selected from the group consisting of glucose, fructose, galactose, sucrose, sorbitol, and lactose, the starch is selected from the group consisting of tapioca starch, corn starch, potato starch, and arrowroot starch, and the protein is selected from the group consisting of bovine, porcine, and piscine gelatin.

10. A microcapsule of one or more carotenoids comprising a protective coating of a carotenoid composition substantially free of oil or fat and that releases the carotenoids upon ingestion of the microcapsule and wherein the carotenoid content of the microcapsule is between about 5% and about 20% by weight.

11. A microcapsule as defined in claim 10, wherein the carotenoid composition is less than 40% oil or fat.

* * * * *